(12) United States Patent
Iwase et al.

(10) Patent No.: US 7,534,232 B2
(45) Date of Patent: May 19, 2009

(54) INDWELLING NEEDLE

(75) Inventors: Yosiharu Iwase, Tokyo (JP); Yasuhiro Yamaguchi, Tokyo (JP)

(73) Assignee: Nipro Corporation, Osaka-Shi, Osaka (JP)

(*) Notice: Subject to any disclaimer, the term of this patent is extended or adjusted under 35 U.S.C. 154(b) by 0 days.

(21) Appl. No.: 11/650,333

(22) Filed: Jan. 5, 2007

(65) Prior Publication Data

US 2008/0167623 A1 Jul. 10, 2008

(51) Int. Cl.
*A61M 5/32* (2006.01)

(52) U.S. Cl. ...................... 604/198; 604/192

(58) Field of Classification Search .............. 604/198, 604/164.08, 192, 263, 264; 128/919
See application file for complete search history.

(56) References Cited

U.S. PATENT DOCUMENTS

| 2002/0120215 A1* | 8/2002 | Crawford et al. ............. 600/573 |
| 2004/0044313 A1* | 3/2004 | Nakajima .............. 604/167.02 |
| 2007/0016148 A1* | 1/2007 | Iwase et al. .................. 604/264 |
| 2007/0185456 A1* | 8/2007 | Nakajima .............. 604/164.08 |

FOREIGN PATENT DOCUMENTS

| EP | 1475124 A1 * | 11/2004 |
| JP | 10-085333 | 4/1998 |
| JP | 2002-330945 | 11/2002 |
| JP | 2003-180829 | 7/2003 |

* cited by examiner

*Primary Examiner*—Kevin C Sirmons
*Assistant Examiner*—Bhisma Mehta
(74) *Attorney, Agent, or Firm*—Flynn, Thiel, Boutell & Tanis, P.C.

(57) ABSTRACT

Indwelling needle composed of a body having a closed end, a needle forming at the tip a sharp edge, a tubular hub retaining the proximal end of the needle and slidable along the main body, a protective cover slidable along the main body and projecting from the main body, and a spring elastically fitted between the body and the protective cover.

When a first projection is lifted by actuating a lever provided on the body and retractable along with the protective cover relative to the body, the first projection is housed in a through hole and presses a second projection of the protective cover engaged with a second engaging portion toward the inner circumference, rendering an operative state.

The resultant length of indwelling needle in operative state can be modified, inhibiting injury to patient.

8 Claims, 2 Drawing Sheets

INDWELLING NEEDLE

BACKGROUND OF THE INVENTION

1. Field of the Invention

The present invention relates to an indwelling needle, and specifically relates to the indwelling needle which stores a needle in a protective cover in a housed state.

2. Description of the Related Art

Presently, puncturing of a patient with a indwelling needle is performed for intravenous drip, dialysis, or the like, on which occasion it is required to prevent a healthcare professional being accidentally punctured with the indwelling needle withdrawn from the patient.

For this reason, there has been known the indwelling needle provided with a needle having a sharp edge formed at the tip thereof, a tubular hub for retaining the proximal end of the needle, and a tubular protective cover slidably provided along the needle (Patent Documents 1-3).

The indwelling needle of Patent Document 1 (Japanese Patent Laid-Open No. 10-85333) is constituted with the hub for retaining the proximal end of a cannula and a retention tube for housing and retaining the hub therein. The cannula is housed in the retention tube by sliding the retention tube.

The indwelling needle of Patent Document 2 (Japanese Patent Laid-Open No. 2002-330945) is constituted with the hub provided at the proximal end of a needle cannula and a safety shield for slidably housing the hub. A spring elastically fitted between the hub and the safety shield extends by operating an actuator from a use state so that the needle cannula is housed in the safety shield.

The indwelling needle of Patent Document 3 (Japanese Patent Laid-Open No. 2003-180829) is constituted with a needle assembly, including the needle cannula and a needle hub, and a body for slidably housing the needle assembly. A puncturing element is housed in the body with elastic force of a spring by operating an operation button when medical treatment is completed.

As described above, according to the indwelling needles of Patent Documents 1-3, a housed state in which the needle is housed in the protective cover is achieved after use, thereby the accident mentioned above is prevented.

However, in the cases of the indwelling needles of the Patent Documents 1-3, the length of the protective cover requires to be set longer than the length that the needle projects from the protective cover, so that the length of a member fixed to a patient in the use state must be set long.

In this case, if used for the patient who is undergoing dialysis therapy, tissue of a punctured site is hardened by being punctured with the needle for many times and forms a knobby swelling. If the member fixed to the patient in the use state is long in length, the indwelling needle touches the swelling when the indwelling needle is fixed to the patient and the angle of the needle inserted in a blood vessel is displaced, which may cause pain to the patient.

In addition, since the Patent Documents 2 and 3, take constitution that the elastic force of the spring retracts the hub relative to the body until the needle is housed in the protective cover, the blood vessel may be damaged by the needle being rapidly withdrawn from the blood vessel and the blood or body fluid adhered to the interior or surface of the needle may splatter.

SUMMARY OF THE INVENTION

In view of such problems, the present invention provides an indwelling needle in which a member fixed to an attaching object is short in length in a use state. And the present invention also provides an indwelling needle which can prevent a blood vessel from being damaged or blood from being splattered.

That is, the indwelling needle according to the present invention is characterized in that there is provided a needle having a sharp edge formed at the tip thereof, a tubular hub for holding the needle, and a tubular protective cover surrounding the needle and slidable along the needle, the indwelling needle being switchable between a use state in which the protective cover is relatively moved toward the proximal end of the needle in an axial direction so that the sharp edge of the needle projects from the protective cover and a housed state in which the protective cover is relatively moved toward the tip of the needle in the axial direction so that the sharp edge of the needle is housed in the protective cover, wherein the hub has a tubular body slidably provided therein, the body having the protective cover slidably provided therein so that the needle slidably passes through the body and the protective cover, while a spring is elastically fitted between the body and the protective cover so as to bias the body and the protective cover toward the proximal end and the distal end, respectively, further comprising a first retention mechanism between the body and the hub for retaining the hub and the needle in the use state in which the hub and the needle is advanced toward the distal end relative to the body, and a second retention mechanism between the body and the protective cover for retaining the protective cover in the use state in which the protective cover is retracted toward the proximal end relative to the body against elastic force of the spring, and the second retention mechanism is released by releasing the first retention mechanism so that the hub is retracted relative to the body into the housed state, thereby the protective cover is advanced relative to the body with the elastic force of the spring to achieve the housed state.

DETAILED DESCRIPTION OF THE PREFERRED EMBODIMENTS

Figure 1:
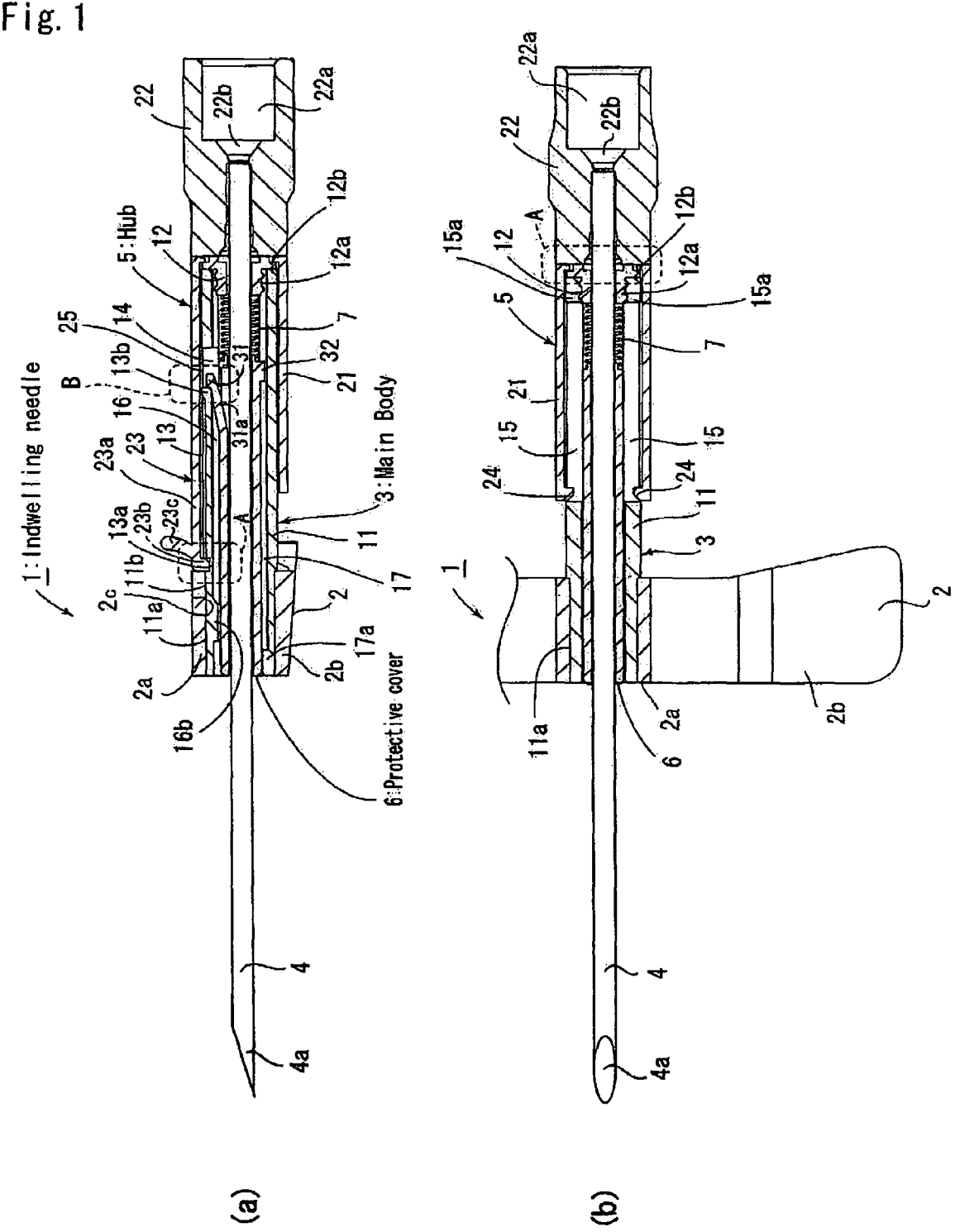
FIG. 1 illustrates an indwelling needle 1 in a use state according to this embodiment, wherein (a) is a sectional view when viewed from a side face direction and (b) is a sectional view when viewed from a top face direction.
Figure 2:
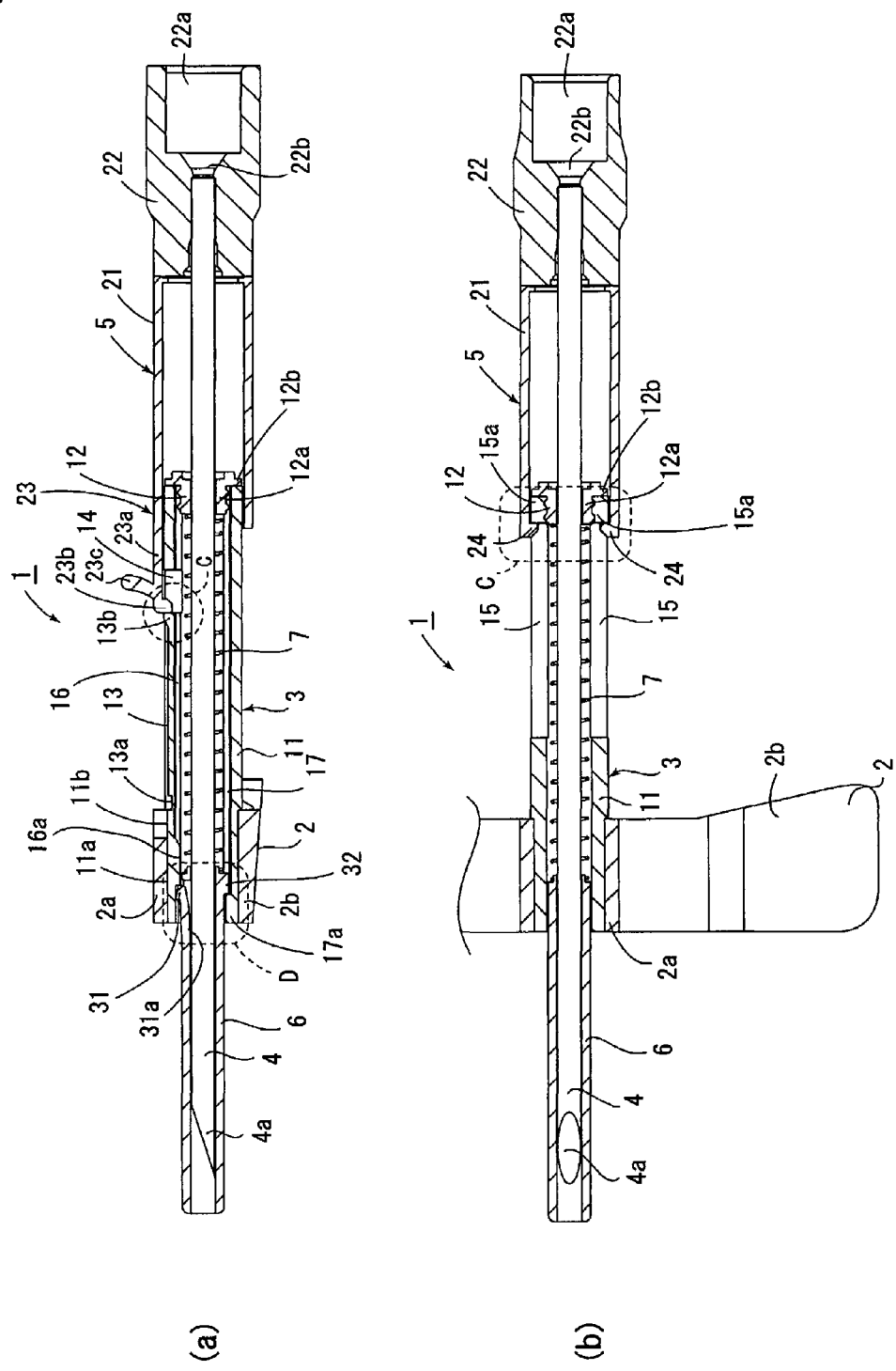
FIG. 2 illustrates the indwelling needle 1 in a housed state according to this embodiment, wherein (a) is a sectional view when viewed from a side face direction and (b) is a sectional view when viewed from a top face direction.

In describing this embodiment hereinbelow, FIGS. 1 and 2 illustrate an indwelling needle 1 according to the present invention, wherein FIGS. 1 and 2 represent sectional views of the indwelling needle 1 in a use state and a housed state, respectively. And FIGS. 1(*a*) and 2(*a*) represent sectional views when viewed from a side face direction while FIGS. 1(*b*) and 2(*b*) represent sectional views when viewed from a top face direction. In the following description, a sharp edge 4*a* side of a needle 4, which is described below, is considered as the distal end.

The indwelling needle 1 of this embodiment is constituted with a wing-shaped member 2 fixed to a patient as an attaching object, a tubular main body 3 fixed to the patient via the wing-shaped member 2, a hollow needle 4 with which a sharp edge 4*a* is formed at the tip, a tubular hub 5 retaining the proximal end of the needle 4 and sliding at the proximal end of the main body 3, a tubular protective cover 6 slidably housed in the main body 3, and a spring 7 elastically fitted between the main body 3 and the protective cover 6.

A use state of the indwelling needle 1 means the state that the hub 5 is positioned at an distal end relative to the main body 3 so that the needle 4 projects from the front end of the main body 3, and that the protective cover 6 is positioned at a proximal end relative to the main body 3 so that the protective cover 6 is housed in the main body 3.

In this use state, the patient is punctured with the sharp edge 4a of the needle 4, and the main body 3 along with the wing-shaped member 2 is fixed to the patient by an adhesive tape or the like.

On the other hand, a housed state of the indwelling needle 1 means the state that the hub 5 is positioned at the proximal end relative to the main body 3 so that the needle 4 is retracted further than the front end of the main body 3, and that the protective cover 6 is projected from the main body 3 so that the needle 4 is housed in the protective cover 6.

In this housed state, the needle 4 is housed in the protective cover 6 when infusion or the like to the patient is completed, so as to prevent an accident that a healthcare professional is punctured with the sharp edge 4a.

The indwelling needle 1 of this embodiment is further provided with, a first retention mechanism A for retaining the main body 3 and the hub 5 in the use state, a second retention mechanism B for retaining the main body 3 and the protective cover 6 in the use state, a third retention mechanism C for retaining the main body 3 and the hub 5 in the housed state, and a fourth retention mechanism D for retaining the main body 3 and the protective cover 6 in the housed state.

The wing-shaped member 2 is constituted with a cylindrical portion 2a surrounding the main body 3 and a wing portion 2b extending at both sides of the cylindrical portion 2a, wherein a groove 2c for preventing from rotation is formed on an upper portion (upper portion of FIG. 1(a)) of the cylindrical portion 2a.

The wing portion 2b is deformed to conform to the skin of the patient and the surface of the wing-shaped member 2 is fixed by the adhesive tape or the like, so that the indwelling needle 1 is fixed to the patient.

The main body 3 is constituted with a cylindrical part 11 having a substantially cylindrical shape and a cap 12 screwed to the proximal end of the cylindrical part 11.

At the front end of the cylindrical part 11, there is formed a connecting part 11a in which the cylindrical portion 2a of the wing-shaped member 2 is fitted. Rotation of the wing-shaped member 2 and the main body 3 relative to each other is prevented by fitting the groove 2c of the cylindrical portion 2a in a projecting shape 11b formed over the connecting part 11a.

On the outer periphery of the cylindrical part 11, there are formed a first guide groove 13 (see FIG. 2(a)) from the front end toward the proximal end, a first engaging portion 13a caved in toward the inner periphery at the front end of the first guide groove 13, a second engaging portion 13b projecting toward the outer periphery at the proximal end, and a through hole 14 at the proximal end of the second engaging portion 13b.

First guide holes 15 are drilled in the both sides of the cylindrical part 11 from the front end toward the proximal end, wherein the proximal ends of the first guide holes 15 each serves as a third engaging portion 15a.

On the inner periphery of the cylindrical part 11, a second guide groove 16 and a third guide groove 17 are formed from the front end toward the proximal end at the upper and lower portions, respectively.

These second and third guide grooves 16 and 17 are provided with fourth and fifth engagement sections 16a and 17a projecting toward inside at their distal ends, respectively, wherein the fifth engagement section 17a is formed at the front end of the third guide groove 17 and the fourth engaging portion 16a is formed closer to the proximal end than the fifth engagement section 17a.

The cap 12 is constituted by a sliding section 12a slidably retaining the needle 4 while screwed in the proximal end of the cylindrical part 11 and a lid 12b formed at the proximal end of the sliding section 12a while contacting with the proximal end of the cylindrical part 11.

The front end of the sliding section 12a constitutes the bottom of the main body 3, while the proximal end of the spring 7 is made into contact with the front end of the sliding section 12a for being biased toward the proximal end by the elastic force of the spring 7.

The hub 5 is constituted by a cylindrical portion 21 for housing the main body 3 and a retaining portion 22 fixed to the proximal end of the cylindrical portion 21 and retaining the proximal end of the needle 4, to which a non-illustrated infusion tube is connected.

The cylindrical portion 21 has a closed end, in which the needle 4 passes through at the center and the lid 12b of the cap 12 contacts therewith. At the front end of the cylindrical portion 21, there is provided an actuating lever 23 for maintaining and canceling the use state.

At the front end of the cylindrical portion 21, third projections 24 projecting toward the inner circumference are formed on both sides thereof, wherein the third projections 24 move along the first guide holes 15 formed on the main body 3 while preventing the hub 5 and the main body 3 from rotating relative to each other.

At the upper portion of the inner periphery of the cylindrical portion 21, a fourth guide groove 25 is formed from the front end toward the proximal end, so that the second engaging portion 13 of the main body 3 slides along the fourth guide groove 25 while the fourth guide groove 25 prevents the hub 5 and the main body 3 from rotating relative to each other.

The actuating lever 23 is constituted with a flexible arm 23a, a first projection 23b provided at the distal end of the arm 23a while moving along the first guide groove 13 of the main body 3, and a tab 23c provided at the upper portion of the first projection 23b.

The arm 23a elastically deforms and the first projection 23b is fitted in the first engaging portion 13a in the use state. When the arm 23a is elastically deformed from this state by pulling up the tab 23c, the first projection 23b can be disengaged from the first engaging portion 13a.

The proximal end of the cylindrical portion 21 and the front end of the retaining portion 22 are fixed to each other, and a liquid passage 22b is formed in the retaining portion 22 between the needle 4 and the connecting part 22a to which the infusion tube is connected. Therefore the infusion solution flowing in via the infusion tube is supplied to the needle 4 through the liquid passage 22b.

Next, the protective cover 6 is slidably housed in the inner periphery of the main body 3 so that the front end thereof is aligned with the front end of the main body 3 in the use state.

A second projection 31 which moves along the second guide groove 16 of the main body 3 is formed at the upper portion of the protective cover 6. A fourth projection 32 which moves along the third guide groove 17 of the main body 3 is formed at the lower portion of the protective cover 6.

The second projection 31 is provided at the proximal end of a flexible deforming section 31a projecting from the distal end toward the proximal end. The deforming section 31a elastically deforms when the second projection 31 is pressed toward the inner periphery.

In describing the first retention mechanism A for retaining the main body 3 and the hub 5 of the indwelling needle 1 in the use state, when the hub 5 is positioned at the distal end relative to the main body 3 in FIG. 1, the lid 12b of the cap 12 of the main body 3 comes into contact with the bottom of the cylindrical portion 21 of the hub 5 so that the first projection 23b of the actuating lever 23 of the main body 3 is inserted into the first engaging portion 13a of the first guide groove 13 of the main body 3.

At this time, the end face at the proximal end of the first projection 23b engages with the end face at the distal end of the first engaging portion 13a, thereby, the use state of the main body 3 and the hub 5 is retained with holding the hub 5 so as not to be retracted relative to the main body 3.

Next, in describing the second retention mechanism B for retaining the main body 3 and the protective cover 6 in the use state, when the protective cover 6 is positioned at the proximal end relative to the main body 3 in FIG. 1, the front end of the protective cover 6 and the front end of the main body 3 aligns so that the second projection 31 is inserted into the through hole 14 of the main body 3.

At this time, the end face at the distal end of the second projection 31 engages with the end face at the proximal end of the second engaging portion 13b, thereby the protective cover 6 is retained so as not to be advanced against the elastic force of the spring 7, retaining the use state of the main body 3 and the protective cover 6.

Next, in describing the third retention mechanism C for retaining the main body 3 and the hub 5 in the housed state, the hub 5 is in a state moved to the proximal end relative to the main body 3 in FIG. 2.

At this time, the first projection 23b of the actuating lever 23 is inserted into the through hole 14 of the main body 3 and the end face at the distal end of the first projection 23b engages with the end face at the proximal end of the second engaging portion 13b, so as to restrain the hub 5 from being advanced relative to the main body 3, preventing from being returned to the use state.

In the housed state, the third projection 24 formed on the cylindrical portion 21 of the hub 5 is positioned at the proximal end of the first guide hole 15 of the main body 3, and the end face at the proximal end of the third projection 24 engages with the end face at the distal end of the third engaging portion 15a, thereby the hub 5 is retained so as not to further fall off from the main body 3.

As described above, by engaging the first projection 23b formed on the hub 5 with the first engaging portion 13a formed on the main body 3 and engaging the third projection 24 formed on the hub 5 with the third engaging portion 15a formed on the main body 3, the main body 3 and the hub 5 can be retained in the housed state.

In describing the fourth retention mechanism D for retaining the main body 3 and the protective cover 6 in the housed state, the protective cover 6 is moved to the distal end relative to the main body 3 and the needle 4 is housed in the protective cover 6 in FIG. 2.

At this time, the second projection 31 of the protective cover 6 is positioned closer to the distal end than the fourth engaging portion 16a of the second guide groove 16 of the main body 3, thereby the end face at the proximal end of the second projection 31 engages with the end face at the distal end of the fourth engaging portion 16a, so as to restrain the protective cover 6 from being retracted, preventing from being returned to the use state.

On the other hand, the fourth projection 32 of the protective cover 6 is positioned at the proximal end of the fifth engagement section 17a formed in the third guide groove 17 of the main body 3, and the end face at the distal end of the fourth projection 32 engages with the end face at the proximal end of the fifth engagement section 17a, preventing the protective cover 6 from falling off from the main body 3.

As described above, by engaging the second projection 31 formed on the protective cover 6 with the fourth engaging portion 16a formed on the main body 3 and engaging the fourth projection 32 formed on the protective cover 6 and the fifth engagement section 17a formed on the main body 3, the main body 3 and the protective cover 6 can be retained in the housed state.

A method of using the indwelling needle 1 of this embodiment having the constitution above is described.

First, the indwelling needle 1 is used in the use state above, wherein the infusion tube is preliminarily connected to the connecting part 22a of the hub 5, and the needle 4 is covered with a non-illustrated cover at the outer circumference until puncturing the patient with the needle 4.

Next, the cover is removed to puncture the blood vessel of the patient with the needle 4 and the wing-shaped member 2 is deformed to conform to the skin of the patient, followed by the wing-shaped member 2 being fixed to the patient by a tape or the like to fix the indwelling needle 1 to the patient.

Then, the infusion solution from the infusion tube is supplied to the patient via the liquid passage 22b formed in the retaining portion 22 and the needle 4.

When the infusion is completed, the tab 23c of the actuating lever 23 is lifted and moved toward the proximal end relative to the main body 3 by the healthcare professional while the wing-shaped member 2 is fixed to the patient.

Thereby, the arm 23a of the actuating lever 23 is elastically deformed so that the first projection 23b is disengaged from the first engaging portion 13a of the main body 3 and retracted along the first guide groove 13.

When the first projection 23b passes through a slope formed on the second engaging portion 13b of the first guide groove 13 and over the second engaging portion 13b, the arm 23a of the actuating lever 23 is restored from an elastically deformed state and the first projection 23b is inserted into the through hole 14 formed in the main body 3.

As a result, the end face at the distal end of the first projection 23b comes into contact with the end face at the proximal end of the second engaging portion 13b, restraining the hub 5 from being advanced relative to the main body 3.

On the other hand, when the hub 5 is retracted relative to the main body 3, the third projection 24 formed on the hub 5 is retracted along the first guide hole 15, while the hub 5 is not retracted further when contacting with the third engaging portion 15a.

In this manner, the main body 3 and the hub 5 are retained in the housed state by the third retention mechanism C, and, by achieving such a state, the needle 4 is withdrawn from the patient by a movement amount of the hub 5 from the main body 3 fixed to the patient with the wing-shaped member 2.

Since this movement of the hub 5 is performed by the healthcare professional, the needle 4 is prevented from being rapidly withdrawn from the blood vessel, so that it can prevent the blood vessel from being damaged.

It is not necessary to withdraw the sharp edge 4a completely from the blood vessel at this time.

In this manner, the hub 5 and the main body 3 is retained in the housed state by the third retention mechanism C while the first projection 23b is inserted into the through hole 14, thereby the first projection 23b presses the second projection 31 of the protective cover 6 from above.

The elastic force of the deforming section 31a for retaining the second projection 31 is set low relative to the force of the arm 23a of the actuating lever 23 being restored from the elastically deformed state, so that the second projection 31 moves toward the inner periphery when the first projection 23b presses the second projection 31, thereby an engaged state of the second projection 31 and the second engaging portion 13b is released, releasing the second retention mechanism B.

Then, by the spring 7 elastically fitted between the protective cover 6 and the main body 3, the protective cover 6 and the main body 3 move away from each other. At this time, since the main body 3 is fixed to the patient, the protective cover 6 is advanced relative to the main body 3.

While the protective cover 6 is advanced, the arm 23a of the second projection 31 is elastically deformed toward the inner periphery, and when the second projection 31 passes through a slope of the fourth engaging portion 16a of the second guide groove 16 and over the fourth engaging portion 16a, the deforming section 31a is restored from the elastically deformed state, so that the second projection 31 projects toward the outer circumference again and is positioned at the distal end of the fourth engaging portion 16a.

Thereby, the end face at the proximal end of the second projection 31 and the end face at the distal end of the fourth engaging portion 16a come to be engaged, so that the protective cover 6 is not retracted relative to the main body 3, restraining them from being returned to the use state.

Moreover, the fourth projection 32 moves along the third guide groove 17 of the main body 3, and, when the end face at the distal end of the fourth projection 32 engages with the end face at the proximal end of the fifth engagement section 17a of the third guide groove 17, the protective cover 6 is not further advanced relative to the main body 3, restraining the protective cover 6 from falling off from the main body 3.

Thereby, the protective cover 6 and the main body 3 are retained in the housed state by the fourth retention mechanism D at a housed state.

In this manner, the second retention mechanism B for retaining the protective cover 6 and the main body 3 in the housed state is released when the main body 3 and the hub 5 are retained in the housed state, and then the protective cover 6 is advanced by biasing force of the spring 7.

For this reason, the needle 4 can be housed in the protective cover 6 projecting relative to the main body 3 when the needle 4 is withdrawn from an arm of the patient, resulting in that the blood or body fluid adhered to the interior or surface of the needle 4 can be prevented from splattering.

According to the indwelling needle 1 of this embodiment having such constitution, the member which contacts with the patient in the use state can be shortened in length.

Specifically, by positioning the hub 5 at the distal end relative to the main body 3 and housing the proximal end of the main body 3 in the hub in the use state, the needle 4 projecting from the front end of the main body 3 can be lengthened while a part thereof contacting with the patient can be shortened in length.

Although the hub 5 is relatively moved to the proximal end relative to the main body 3 when the housed state is achieved and a part contacting with the patient becomes longer due to the main body 3 being exposed from the hub 5, the housed state is maintained for only a short period while the indwelling needle 1 is withdrawn from the patient, so that it does not cause a burden for the patient.

When switched from the use state to the housed state, the hub 5 is first retracted relatively to the main body 3 by the healthcare professional, so that the needle 4 can be withdrawn from the patient without using the elastic force of the spring 7, inhibiting damage to the blood vessel.

Since the use state of the protective cover 6 and the main body 3 is released (the second retention mechanism B is released) when the hub 5 and the main body 3 are retained in the housed state by the third retention mechanism C, the protective cover 6 can be advanced by the force of the spring 7 while the needle 4 has been withdrawn, housing the needle 4 in the protective cover 6.

At this time, the hub 5 is retracted relative to the main body 3, so that the blood adhered to the interior or surface of the needle 4 can be prevented from splattering even when the protective cover 6 projects to house the needle 4, and the accident that the healthcare professional is punctured with the needle 4 can be prevented by the needle 4 being housed in the protective cover 6.

What is claimed is:

1. An indwelling needle composed of a needle having a sharp edge formed a tip of a distal end thereof, a tubular hub for holding the needle at a proximal end thereof, and a tubular protective cover surrounding and slidable along the needle, the indwelling needle being switchable between a use state in which the protective cover is relatively moved toward the proximal end of the needle in an axial direction thereof so that the sharp edge of the needle projects from the protective cover and a housed state in which the protective cover is relatively moved toward the distal end of the needle in the axial direction thereof so that the sharp edge of the needle is housed in the protective cover, said indwelling needle comprising:

a tubular body for being fixed to an attaching object such that the tubular body slidably retains the protective cover and the hub in the needle's axial direction so that the needle slidably passes through the body and the protective cover, a spring elastically fitted between the body and the protective cover so as to urge the body and the protective cover toward the proximal and distal ends of the needle in the axial direction thereof respectively, a first retention mechanism configured to retain the hub and the needle in a use state, provided between the hub and the body and comprising a first projection projecting from the hub toward the body and having proximal and distal ends, an end face at the proximal end of the first projection in the needle's axial direction being engaged with an end face at a distal end of a first engaging portion in the needle's axial direction formed on the body so as to retain the use state preventing the hub from being retracted relative to the body, whereby the hub and the needle are extended in the needle's axial direction relative to the body, and a second retention mechanism configured to retain the protective cover in the use state, provided between the body and the protective cover and comprising a second projection projecting from the protective cover toward the body and having proximal and distal ends, an end face at the distal end of the second projection in the needle's axial direction being engaged with an end face at a proximal end of a second engaging portion in the needles s axial direction formed on the body so as to retain the use state preventing the protective cover from being advanced relative to the body, whereby the protective cover is retracted toward the proximal end of the needle in the axial direction thereof relative to the body against an elastic force of the spring, the second retention mechanism being released by releasing the first retention mechanism so that the hub and needle are retracted relative to the body in the needle's axial direction by a necessary amount, whereby the protective cover is advanced toward the distal end of the needle in the axial direction thereof relative to the body with the elastic force of the spring to achieve the housed state and the first projection presses the second projection when the hub is retracted relative to the body to release an engaged state of the second projection and the second engaging portion, so that the protective cover is advanced relative to the body by the elastic force of the spring.

2. The indwelling needle according to claim 1, wherein the first projection is provided on a flexible arm provided to the hub, the arm being elastically deformed in needle radial direction to release engagement of the end face at the proximal end of the first projection in the axial direction and the end face at the distal end of the first engaging portion in the axial direction, and the first projection presses the second projection to release the engaged state of the second projection and the second engaging portion by the elastic force of the elastically deformed arm being restored to an original shape thereof.

3. The indwelling needle according to claim 1, further comprising a third retention mechanism for restraining the hub from being advanced relative to the body to retain the housed state when the hub and the body are made into the housed state, the third retention mechanism comprising an end face at the distal end of the first projection and the end face at the proximal end of the second engaging portion, the end face at the distal end of the first projection being engaged with the end face at the proximal end of the second engaging portion to restrain the hub from being advanced relative to the body when the hub is in the housed state.

4. The indwelling needle according to claim 3, wherein the third retention mechanism comprises a third projection formed on either one of the hub and the body and a third engaging portion formed on the other one of the hub and the body, the third projection being engaged with the third engaging portion when the hub is retracted relative to the body to achieve the housed state, restraining the hub from being retracted relative to the body.

5. The indwelling needle according to claim 1, further comprising a fourth retention mechanism for restraining the protective cover from being retracted relative to the body to retain the housed state when the protective cover and the body are made into the housed state, the fourth retention mechanism comprising an end face at the proximal end of the second projection and a fourth engaging portion formed on the body, the end face at the proximal end of the second projection being engaged with a front end face of the fourth engaging portion to restrain the protective cover from being retracted relative to the body when the protective cover is in the housed state.

6. The indwelling needle according to claim 5, wherein the fourth retention mechanism comprises a fourth projection formed on either one of the protective cover and .the body and a fifth engagement section formed on the other one of the protective cover and the body, the fourth projection being engaged with the fourth engaging portion when the protective cover is advanced relative to the body to achieve the housed state, restraining the protective cover from being advanced relative to the body.

7. The indwelling needle according to claim 1, wherein the body comprises a cylindrical part for housing the protective cover and a cap formed at a proximal end of the cylindrical part, through which the needle slidably passes, and wherein the spring is elastically fitted between a proximal end of the protective cover and the cap.

8. The indwelling needle according to claim 1, wherein the body comprises a wing-shaped member for fixing the body to the attaching object.

* * * * *